United States Patent [19]

van der Weerdt et al.

[11] 4,448,712
[45] May 15, 1984

[54] PERFUME COMPOSITIONS AND PERFUMED ARTICLES CONTAINING SPIRO-UNDECANONES AND -UNDECENONES AS PERFUME BASE

[75] Inventors: Antonius J. A. van der Weerdt, Huizen; Willem Apeldoorn, Blaricum, both of Netherlands

[73] Assignee: Naarden International N.V., Ca Naarden-bussum, Netherlands

[21] Appl. No.: 417,207

[22] Filed: Sep. 13, 1982

[30] Foreign Application Priority Data

Sep. 16, 1981 [NL] Netherlands .................. 8104271

[51] Int. Cl.$^3$ .................. C11B 9/00; A01K 7/46; C07C 49/317
[52] U.S. Cl. .................. 252/522 R; 568/367; 568/345; 252/174.11
[58] Field of Search .................. 252/522 R; 568/367

[56] References Cited

U.S. PATENT DOCUMENTS 3,923,873 12/1975 Maurer et al. .................. 560/231
4,052,457 10/1977 Nagakura et al. .................. 568/349
4,203,925 5/1980 Barton et al. .................. 568/362
4,261,866 4/1981 Barton et al. .................. 568/367

FOREIGN PATENT DOCUMENTS 74693 3/1983 European Pat. Off. ......... 252/522 R
1343916 6/1971 United Kingdom .
1343915 6/1971 United Kingdom .

OTHER PUBLICATIONS

Rice, L. M. et al., Spiranes X Aminospiranes, pp. 825–829, "Journal of Medicinal Chemistry", vol. 8, Nov. 1965.
Kane, V., "A General and Efficient Approach to Spirocyclohexadienones", *Synthetic Communications*, 6(3), 237–242, (1976).
Christol, H. et al., "Condensation d'aldoenamines cyclaniques avec la methylvinylcetone", Bulletin de la Societe Chimique di France, (1970) No. 12, p. 4468.
Martin, Stephen, "Carbonyl Homologation with α Substitution., A New Approach to Spiroannelation", J. Org. Chem., vol. 41, No. 20, 1976.
de Jongh, H. A. P. et al., "Spiranes III", Tetrahedron, 1964, vol. 20, pp. 2553–2573.

Primary Examiner—Anton H. Sutto
Attorney, Agent, or Firm—Brumbaugh, Graves, Donohue & Raymond

[57] ABSTRACT

Perfume compositions, perfumed materials and perfumed articles containing derivatives of spiro [5.5] undecane-3-one and/or undecene-3-one having the following formula

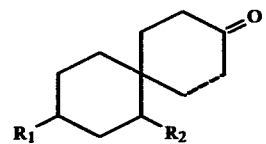

(1)

wherein $R_1$ and $R_2$ are hydrogen or methyl and the dotted line is a single or double bond with the provisio that when this dotted line is a double bond $R_1$ and $R_2$ are both hydrogen.

The use of one or more derivatives of spiro [5.5] undecane-3-one and /or -undecene-3-one having formula 1 as a perfume component in perfume compositions and in imparting fragrance to materials and articles for example soaps, cleaning preparations and cosmetic preparations.

5 Claims, No Drawings

PERFUME COMPOSITIONS AND PERFUMED ARTICLES CONTAINING SPIRO-UNDECANONES AND -UNDECENONES AS PERFUME BASE

The invention relates to perfume compositions containing spiro-undecanone derivatives and spiro-undecenone derivatives as perfume base, to articles perfumed with these compounds respectively with perfume compositions containing these compounds and to new spiro-undecanones.

There is a continuing interest in the preparation and application of synthetic fragrances because these fragrances always can be prepared in the quantity desired and with uniform quality, contrary to the naturally occurring substances. In particular there is a large demand for synthetic frequences having a characteristic natural odor. Moreover, for some applications like perfuming of modern detergents a high chemical stability is required.

It has been found that derivatives of spiro[5.5.]undecane-3-one and -undecene-3-one having the formula

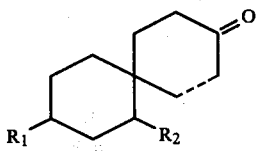

(1)

in which $R_1$ and $R_2$ are a hydrogen atom or a methyl group and the dotted line is a carbon-carbon single or double bond with the provisio that when this dotted line is a double bond $R_1$ and $R_2$ are both a hydrogen atom, are valuable fragrances having a somewhat fruity and spicy odor which also strongly resembles to irises.

Only little is known about the olfactory properties of spiro ketones. However, in U.S. Pat. No. 3,923,837 it is mentioned that several 6.10-dialkylspiro[4,5]decane-2-ones and -decane-8-ones and corresponding dec-6-enones are usable as fragrances and flavourings and are characterized by woody, earthy and balsamic odor notes remembering to ambergris, ylang, sandalwood and patchlouli. Further U.S. Pat. No. 4,203,925 discloses a number of alkyl substituted spiro[4,5] decane-8-ones, -decene-8-ones and -decadiene-8-ones, which are familiar with β-vetivone (2-isopropylidene-6,10-dimethylspiro[4,5]dec-6-ene-8-one), a component of vetiver oil. These compounds also have woody and earthy odors. So the compounds disclosed in the above mentioned U.S. patent numbers are from a chemical point of view as well as with respect to the olfactory properties very different from the compounds according to the present invention.

It is emphasized that the use of derivatives of spiro-undecane and -undecene and in particular of spiro[5,-5]undecane and -undecene is completely unknown in the perfume industry. On the other hand the undermentioned compounds having the formulas 1a, 1b and 1c are known per se and are described in the literature mentioned therewith. So no exclusive rights are claimed for these compounds as such. Further no olfactory properties of these known compounds are known.

(1a) Spiro[5,5]undecane-3-one

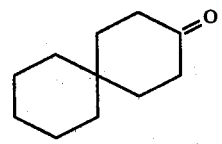

(1a)

H. A. P. de Jongh and H. Wijnberg, Tetrahedron 20, 2553–73 (1964);
British patent specifications Nos. 1,343,915 and 1,343,916.

(1b) Spiro[5,5]undec-1-ene-3-one.

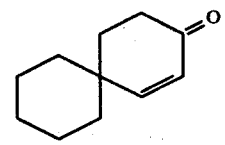

(1b)

H. Cristol, F. Plenat and J. Salancon, Bull. Soc. Chim. France 1970, 4468–71;
V. V. Kane, Synth. Commun. 6, 237–42 (1976);
S. F. Martin, J. Org. Chem. 41, 3337–8 (1976).

(1c) 9-Methyl-spiro[5.5]undecane-3-one.

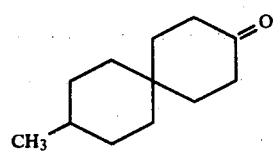

(1c)

L. M. Rice, E. C. Dobbs and C. H. Grogan, J. Med. Chem. 8, 825–9 (1965) vide Chem. Abstract 63 16227e.

The compounds 7-methyl-spiro[5.5]undecane-3-one having the formula

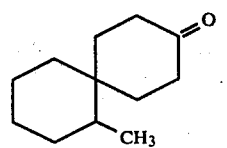

(1d)

and 7.9-dimethyl-spiro[5.5]undecane-3-one having the formula

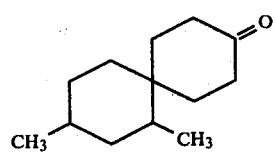

(1e)

are new.

The compounds according to the invention can be prepared according to the methods described in the literature especially in the references mentioned for the compound having formula (1b). The most known method is illustrated in the following reaction scheme:

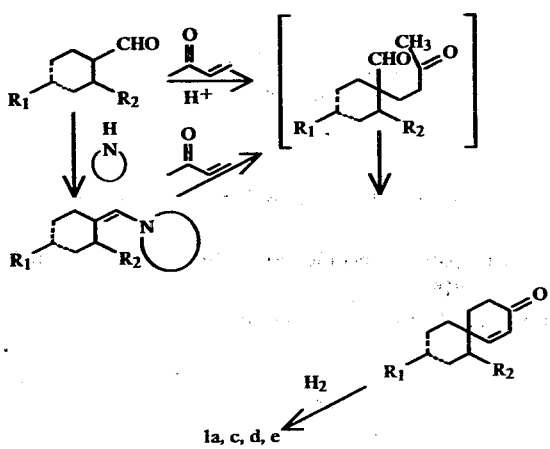

in which the dotted lines are single bonds or at most one double bond. According to this method a suitable cyclohexene- or cyclohexane carbaldehyde, optionally as enamine, is reacted with methylphenyl ketone followed by a cyclisation of the formed ketoaldehyde via an intramolecular aldol condensation. This last stage often goes spontaneously. When the route via the enamine is followed each secondary amine suitable therefore can be used. Amines which are often used for such reactions are for instance pyrrolidine and morpholine. The double bonds can be removed from the reaction product according to known methods like catalytic hydrogenation.

The spiroketones according to the invention are powerful fragrances having a very natural fruity, spicy odor reminiscent to irises. Especially with the compounds having the formulae 1b, 1d and 1e the irises character comes strongly to the fore whereas with the compound having formula 1a the fruity-spicy character is somewhat more represented. The spiroketones according to the invention can be successfully used in perfume compositions or as such as odor imparting agents. Because of their stability the compounds according to the invention are very suitable for perfuming of agressive media like modern detergents.

The phrase "perfume composition" is used to mean a mixture of fragrances and optionally auxiliary substances that may be dissolved in an appropriate solvent or mixed with a powdery substrate used to impart a desired odor to the skin and/or various products. Examples of said products are: soaps, washing agents, dish washing and cleaning agents, air refreshers and room sprays, pommanders, candles, cosmetics such as creams, ointments, colognes, pre- and after shaving lotions, talcum powders, hair care agents, body deodorants and antiperspirants.

Fragrances and mixtures thereof which in combination with the compounds according to the invention can be used for the preparation of perfume compositions include natural products such as essential oils, absolutes, resinoids, resins, concretes etc., synthetic fragrances, such as hydrocarbons, alcohols, aldehydes, ketones, ethers, acids, esters, acetals, ketals, nitrils etc., both saturated and unsaturated compounds, aliphatic, carbocyclic and heterocyclic compounds.

Fragrances to be used in combination with the compounds according to the invention include geraniol, geranyl acetate, linalool, linalyl acetate, tetrahydrolinalool, citronellol, citronellyl acetate, myrcenol, myrcenyl acetate, dihydro myrcenol, dihydro myrcenyl acetate, tetrahydro myrcenol, terpineol, terpinyl acetate, nopol, nopyl acetate, β-phenyl ethanol, β-phenylethyl acetate, benzyl alcohol, benzyl acetate, benzyl salicylate, benzyl benzoate, amyl salicylate, styrallyl acetate, dimethylbenzyl carbinol, trichloro methylphenylcarbinyl acetate, p-ter.butyl cyclohexyl acetate, isononyl acetate, vetiveryl acetate, vetiverol, α-hexyl cinnamon aldehyde, 2-methyl-3-(p-tert.butyl-phenyl)-propanol, 2-methyl-3-(p-isopropyl phenyl)-propanol, 3-(p-tert.butylphenyl)-propanol, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydro pyran, 3-carboxymethyl-2-pentylcyclopentane, 2-n-heptyl cyclopentanone, 3-methyl-2-pentyl-2-cyclopentanone, n-decanal, n-dodecanal, 9-decenol-1, phenoxyethyl isobutyrate, phenyl acetaldehyde dimethylacetal, phenyl acetaldehyde diethylacetal, geranyl nitril, citronellyl nitril, cedryl acetate, 3-isocamphyl cyclohexanol, cedrylmethyl ether, isolongifolanon, aubepine nitrile, aubepine, heliotropine, coumarine, eugenol, vanilline, diphenyl oxide, hydroxy citronellal, ionones, methyl ionones, isomethyl ionones, irones, cis-3-hexenol and esters thereof, indan musk fragrances, tetraline musk fragrances, isochroman musk fragrances, macrocycli ketones, macrolactone musk fragrances, ethylene brassylate, aromatic nitromusk fragrances.

Auxiliary agents and solvents that may be incorporated into perfumed compositions according to the invention comprise, for example, ethanol, isopropanol, diethyleneglycol monoethylether, diethyl phtalate etc.

The amount of the esters that can be used in a perfume composition or in a perfumed product can be varied within broad limits and depends, for example, on the product wherein the perfume is used, the nature and the amount of the further components of the perfume compositions and the odor effect desired. Therefore, it is only possible to indicate very rough limits. However, these limits will give a person skilled in the art sufficient information concerning the odor strength and possibilities for the use of the compounds according to the invention. In most cases a quantity of only 0.01% in a perfume composition is sufficient to obtain a clearly observable odor effect.

In some cases, however, concentrations of 30% or more may be used in the compositions to impart specific odor effects.

In products perfumed with the aid of perfume compositions according to the invention the concentration is lower and depends on the quantity of the composition used in the product.

The following examples only illustrate the preparation and the use of the compounds according to the invention and do not restrict the invention thereto.

Example I

Preparation of 7-methyl-spiro[5.5]undecane-3-one

A solution of 186 g (1.5 mole) 6-methyl-3-cyclohexene carbaldehyde, 148 g (1.7 mole) morpholine and 500 ml toluene was refluxed under simultaneous azeotropic removal of the formed water. When all the water was distilled off the toluene was removed by evaporation. The residue was brought in a nitrogen atmosphere and then 400 ml ethanol and 119 g (1.7 mole) methylvinyl ketone were added. This mixture was refluxed during 20 hours in a nitrogen atmosphere. After the mixture was cooled off 350 ml of a buffer solution consisting of 2 parts by weight water, 2 parts by weight acetic acid and 1 part by weight sodium acetate. This mixture was refluxed during 2 hours. Then the ethanol was removed by evaporation and the residue was poured out in brine. The mixture was extracted 3 times with ether. The united ether layers were washed alkaline with a 10%'s soda-solution and subsequently washed 1 time with water and dried above MgSO₄. Further the ether was removed by evaporation and the residue was distilled under reduced pressure. Yield: 170 g (65%) 11-methyl-spiro[5.5]undeca-1.8-diene-3-one; boiling point: 115°–117° C./0.7 kPa.

The reaction product was dissolved in 150 ml ethanol after which 2 g 5% Pd/C catalyst was added. The mixture was hydrogenated at 400 kPa and 50° C. until the theoretical amount of hydrogen was taken up. After that the catalyst was removed by filtration and the ethanol removed by evaporation the residue was distilled under reduced pressure. Yield: 162 g (93%) 7-methyl-spiro[5.5]undecane-3-one; boiling point: 117°–118° C./0.7 kPa; $n_D^{25}=1.4935$.

Example II

Preparation of 7.9-dimethyl-spiro[5.5]undecane-3-one

A mixture of 69 g (0.5 mole) 2.4-dimethyl-3-cyclohexene carbaldehyde and 0.5 g p-toluene sulphonic acid was heated at 50°–60° C. During half an hour 35 g (0.5 mole) methyl-vinyl ketone was added after which the mixture was stirred during 4 hours at 60° C. Then 150 ml toluene was added and the formed water was distilled off azeotropically. After cooling off the mixture was poured out in 200 ml 10%'s soda solution. The layers were separated after which the organic layer was washed with brine and dried above MgSO₄. The toluene was removed by evaporation and the residue was distilled under reduced pressure. Yield: 40 g (42%) 7.9-dimethyl-spiro[5.5]undeca-1.8-diene-3-one; boiling point 117°–120° C./0.7 kPa.

The reaction product was hydrogenated as mentioned in example I. Yield: 38.8 g (95%) 7.9-dimethyl-spiro[5.5]undecane-3-on; boiling point: 120°–125° C./0.7 kPa; $n_D^{25}=1.4890$.

This compound was also prepared according to the method mentioned in example I; the yield was 58%.

Example III

A perfume composition for use in detergents was prepared according to the following receipt:

| | |
|---|---|
| α-Pentyl cinnamic aldehyde | 100 parts by weight |
| Terpineol | 90 parts by weight |
| 2-Phenyl ethanol | 75 parts by weight |
| Tetrahydro myrcenol | 70 parts by weight |
| Citronellol | 70 parts by weight |
| 4-Tert.butylcyclohexyl acetate | 70 parts by weight |
| Dihydro myrcenol | 60 parts by weight |
| Lavender oil | 55 parts by weight |
| 6-Acetyl-1-isopropyl-2.3.3.5-tetramethyl indane | 50 parts by weight |
| 4-Acetoxy-3-pentyl-tetrahydropyran | 50 parts by weight |
| Tetrahydro linalool | 40 parts by weight |
| 2-Methyl-3-(p-tert.butylphenyl)-propanal | 40 parts by weight |
| α-Methyl jonon | 40 parts by weight |
| Tricyclodecenyl propionate | 30 parts by weight |
| Heliotropine | 10 parts by weight |
| Coumarine | 10 parts by weight |
| Eugenol | 10 parts by weight |
| 7.9-Dimethyl-spiro [5.5] undecane-3-one (1e) | 30 parts by weight |
| | 900 parts by weight |

Example IV

A perfume composition for talcum powder was prepared according to the following receipt:

| | |
|---|---|
| 2-Phenyl ethanol | 100 parts by weight |
| γ-Methyljonon | 100 parts by weight |
| Acetylcedrene | 70 parts by weight |
| Rosana NB 131* | 70 parts by weight |
| Cedar wood oil Virginia | 50 parts by weight |
| Benzyl acetate | 50 parts by weight |
| Lilas NB 146* | 50 parts by weight |
| Hydroxycitronellal | 40 parts by weight |
| Ylang-Ylang oil | 40 parts by weight |
| Geranium oil Bourbon | 25 parts by weight |
| 4-(4-Hydroxy-4-methylpentyl)-cyclohexene-3-carbaldehyde | 20 parts by weight |
| Muskus Ambrette | 20 parts by weight |
| 3-Isocamphyl cyclohexanol | 20 parts by weight |
| Dimethyl-benzylcarbinyl acetate | 15 parts by weight |
| Coumarine | 5 parts by weight |
| 7-Methyl-spiro [5.5] undecane-3-one (1d) | 25 parts by weight |
| | 700 parts by weight |

*Fragrance bases sold by Naarden International N.V.

We claim:

1. Perfume composition, perfumed material and perfumed article, characterized by a contents of one or more derivatives of spiro[5.5]undecane-3-one and/or -undecene-3-one having the following formula

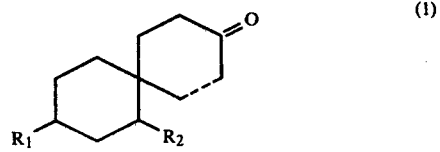

wherein $R_1$ and $R_2$ are hydrogen or methyl and the dotted line is a single or double bond with the provisio that when this dotted line is a double bond $R_1$ and $R_2$ are both hydrogen.

2. Perfume composition according to claim 1, characterized in that the content of the fragrances is at least 0.01% by weight of the concerning derivatives.

3. Application of the perfume composition according to claim 1 or 2 or of one or more derivatives of spiro[5.5]undecane-3-one and/or -undecene-3-one having the formula 1 as such for perfuming of materials and articles.

4. 7-Methyl-spiro[5.5]undecane-3-one.

5. 7.9-Dimethyl-spiro[5.5]undecane-3-one.

* * * * *